(12) United States Patent
Lima et al.

(10) Patent No.: US 12,110,879 B2
(45) Date of Patent: Oct. 8, 2024

(54) ARTIFICIAL MUSCLE ACTUATORS

(71) Applicant: LINTEC OF AMERICA, INC., Plano, TX (US)

(72) Inventors: Marcio Dias Lima, Richardson, TX (US); Yang Yang, Richardson, TX (US); Luis Plata, Richardson, TX (US); Marilu Guerrero, Richardson, TX (US); Franklin Le, Richardson, TX (US); Randy Allen, Richardson, TX (US)

(73) Assignee: LINTEC OF AMERICA, INC., Plano, TX (US)

( * ) Notice: Subject to any disclaimer, the term of this patent is extended or adjusted under 35 U.S.C. 154(b) by 906 days.

(21) Appl. No.: 17/154,391

(22) Filed: Jan. 21, 2021

(65) Prior Publication Data

US 2021/0140414 A1    May 13, 2021

Related U.S. Application Data

(62) Division of application No. 16/467,830, filed as application No. PCT/US2017/065127 on Dec. 7, 2017, now Pat. No. 10,935,009.

(Continued)

(51) Int. Cl.
*F03G 7/06*    (2006.01)
*A61F 2/50*    (2006.01)
(Continued)

(52) U.S. Cl.
CPC ....... *F03G 7/0612* (2021.08); *F03G 7/06146* (2021.08); *F03G 7/067* (2021.08); *F16K 31/44* (2013.01); *H01H 85/04* (2013.01); *H02N 11/006* (2013.01); *H10N 30/857* (2023.02); *A61F 2002/5066* (2013.01);
(Continued)

(58) Field of Classification Search
CPC ..... F03G 7/0612; F16K 31/44; H02N 11/006; H10N 30/857; A61F 2002/5066; H01B 1/18

See application file for complete search history.

(56) References Cited

U.S. PATENT DOCUMENTS

| 3,810,062 A | 5/1974 | Kozacka |
| 3,969,695 A | 7/1976 | Belcher |

(Continued)

FOREIGN PATENT DOCUMENTS

| CN | 101958394 | 11/2011 | | |
| CN | 104520392 A | * 4/2015 | ........... | B65D 83/752 |

(Continued)

OTHER PUBLICATIONS

DE-102012100576-A1_translate (Year: 2013).*

(Continued)

*Primary Examiner* — Tulsidas C Patel
*Assistant Examiner* — Mohammed Ahmed Qureshi
(74) *Attorney, Agent, or Firm* — GREENBLUM & BERNSTEIN, P.L.C.

(57) ABSTRACT

An actuator device that includes a first fiber, a conducting material, and a coating. The coating coats the first fiber or the conducting material. The coating may also provide moisture protection, UV protection, thermal insulation and thermal conductivity.

18 Claims, 5 Drawing Sheets

Related U.S. Application Data

(60) Provisional application No. 62/462,544, filed on Feb. 23, 2017, provisional application No. 62/431,717, filed on Dec. 8, 2016.

(51) Int. Cl.
*F16K 31/44* (2006.01)
*H01H 85/04* (2006.01)
*H02N 11/00* (2006.01)
*H10N 30/857* (2023.01)
*H01B 1/18* (2006.01)

(52) U.S. Cl.
CPC ........ *F03G 7/06114* (2021.08); *F03G 7/0614* (2021.08); *H01B 1/18* (2013.01)

(56) References Cited

U.S. PATENT DOCUMENTS

| | | | |
|---|---|---|---|
| 5,229,739 | A | 7/1993 | Oh |
| 5,963,121 | A | 10/1999 | Stygar |
| 7,692,361 | B2 | 4/2010 | Kato |
| 7,834,527 | B2 | 11/2010 | Alvarez Icaza Rivera |
| 7,935,743 | B1 * | 5/2011 | Rasmussen ............. F03G 7/005 524/916 |
| 8,076,829 | B2 | 12/2011 | Chen et al. |
| 8,434,303 | B2 | 5/2013 | Honda et al. |
| 8,633,795 | B2 | 1/2014 | Knab |
| 9,234,099 | B2 | 1/2016 | Otake |
| 9,425,010 | B2 | 8/2016 | Hentschel |
| 9,863,406 | B2 | 1/2018 | Li et al. |
| 2002/0113684 | A1 | 8/2002 | Arikawa |
| 2003/0139808 | A1 | 7/2003 | Shahinpoor |
| 2004/0104801 | A1 | 6/2004 | Jollenbeck |
| 2006/0125596 | A1 | 6/2006 | Darr |
| 2006/0261709 | A1 | 11/2006 | Kato et al. |
| 2007/0132539 | A1 | 6/2007 | Richter |
| 2010/0060406 | A1 | 3/2010 | Kim |
| 2010/0234779 | A1 | 9/2010 | Asvadi et al. |
| 2010/0296183 | A1 | 11/2010 | Honda et al. |
| 2011/0012476 | A1 | 1/2011 | Chen et al. |
| 2011/0242398 | A1 | 10/2011 | Honda et al. |
| 2011/0279218 | A1 | 11/2011 | Salonga |
| 2014/0132119 | A1 | 5/2014 | Whinnery et al. |
| 2014/0163664 | A1 | 6/2014 | Goldsmith |
| 2015/0191596 | A1 | 7/2015 | Otake |
| 2015/0219078 | A1 | 8/2015 | Li et al. |
| 2016/0025079 | A1 | 1/2016 | Li et al. |
| 2016/0206420 | A1 * | 7/2016 | Yun ........................... A61F 2/08 |

FOREIGN PATENT DOCUMENTS

| | | | | |
|---|---|---|---|---|
| DE | 10 2006 029 693 | A1 | 3/2007 | |
| DE | 102012100576 | A1 * | 7/2013 | ............ B60P 1/5471 |
| EP | 1 693 950 | A1 | 8/2006 | |
| EP | 2 237 093 | | 10/2010 | |
| JP | 56-130054 | A | 10/1981 | |
| JP | 60-77264 | U | 5/1985 | |
| JP | 61-213430 | | 9/1986 | |
| JP | 62-172246 | | 7/1987 | |
| JP | 64-76824 | | 3/1989 | |
| JP | 1-187040 | | 7/1989 | |
| JP | 6-320473 | | 11/1994 | |
| JP | 8-122655 | | 5/1996 | |
| JP | 11-215793 | | 8/1999 | |
| JP | 3062296 | | 9/1999 | |
| JP | 2005-110494 | A | 4/2005 | |
| JP | 2005-176428 | A | 6/2005 | |
| JP | 2006-325335 | A1 | 11/2006 | |
| JP | 2007-159222 | A | 6/2007 | |
| JP | 2007-300714 | A1 | 11/2007 | |
| JP | 2008-100901 | A | 5/2008 | |
| JP | 2009-32773 | A | 2/2009 | |
| JP | 2010-500895 | A | 1/2010 | |
| JP | 2011-125092 | A | 6/2011 | |
| JP | 2011-152031 | A | 8/2011 | |
| JP | 2012-530572 | A | 12/2012 | |
| JP | 2014-34658 | | 2/2014 | |
| JP | 2014-34659 | | 2/2014 | |
| JP | 2016-505790 | | 2/2016 | |
| JP | 2016-42783 | | 3/2016 | |
| JP | 2016-199900 | A | 12/2016 | |
| KR | 101563105 | B1 | 10/2015 | |
| KR | 20160117658 | A | 10/2016 | |
| TW | I553921 | | 10/2016 | |
| WO | 2005/027333 | A1 | 3/2005 | |
| WO | 2009/090960 | | 7/2009 | |
| WO | 2010/073902 | | 7/2010 | |
| WO | 2011/070912 | A1 | 6/2011 | |
| WO | WO2013021638 | | 2/2013 | |
| WO | 2014/022667 | | 2/2014 | |
| WO | 2015/196057 | | 12/2015 | |

OTHER PUBLICATIONS

CN104520392A_translate (Year: 2015).*
Taiwan Official Action and appended Search Report received in TW Patent Application No. 106143208, dated Jun. 22, 2021 and Computer Generated English language translation thereof.
Taiwan Official Action and appended Search Report received in TW Patent Application No. 106143209, dated Jun. 24, 2021 and Computer Generated English language translation thereof.
Notice of Reasons for Rejection received in JP 2019-530463, dated Jun. 14, 2021 and English language translation thereof.
European Office Action recited in European Patent Application No. 17 828 806.4, dated Jun. 25, 2021.
Soheil Kianzad, "A Treatise on Highly Twisted Artificial Muscle: Thermally Driven Shape Memory Alloy and Coiled Nylon Actuators", dated Aug. 2015.
Tawain Office Action and Search Report issued in Application No. 11120032560, dated Jan. 11, 2022.
Japan Official Action received in JP Application No. 2021-087709, dated Mar. 13, 2023.
Notice of Reasons for Rejection received in JP 2021-087709, dated Aug. 1, 2022.
Notice of Allowance received in JP2021-110020, dated Oct. 3, 2022.
Japan Official Action (Notice of Reasons for Rejection) issued in JP 2019-522498, dated Aug. 11, 2020, and English language translation thereof.
U.S. Appl. No. 16/466,532 to Marcio Dias Lima et al., which was filed on Jun. 4, 2019.
U.S. Appl. No. 16/466,131 to Marcio Dias Lima et al., which was filed on Jun. 3, 2019.
Hara, Susumu; Zama Tetsuji, "Conductive Polymer Composite Structural Body Bundle ", Mar. 24, 2005 , Entire Document (Translation of WO 2005027333 ) (of record, cited in the IDS, including Original document). (Year: 2005 ).
Japan Official Action (Decision of Rejection) issued in 2019-524041, dated Mar. 1, 2021 and English language translation thereof.
Japan Notice of Reasons for Rejection in JP Appl. No. 2019-530463, dated Sep. 7, 2020 and English translation.
Japan Notice of Reasons for Rejection in JP Appl. No. 2019-524041, dated Sep. 7, 2020 and English translation.
International Search Report issued in PCT/US2017/065127 mailed on May 14, 2018 (5 pages).
Written Opinion issued in PCT/US2017/065127 mailed on May 14, 2018 (9 pages).
Taiwanese Official Letter issued in Corresponding Taiwanese Patent Application No. 106143209 dated Feb. 10, 2020 (4 pages).
International Search Report issued in PCT/US2017/065151 mailed on May 14, 2018 (6 pages).
Written Opinion issued in PCT/US2017/065151 mailed on May 14, 2018 (8 pages).
Aces Electro materials: "Artificial muscles", XP054978158; Aug. 4, 2015 (Aug. 4, 2015); retrieved from YouTube [online]: URL: http//www.youtube.com/watch?v=vVhUBENOqhg Time frame: 1:21-1:37.

(56) References Cited

OTHER PUBLICATIONS

International Preliminary Report on Patentability issued in Application No. PCT/US2017/065150, mailed on Jun. 20, 2019 (11 pages).
International Search Report issued in PCT/US2017/065127 mailed on Jun. 20, 2019 (10 pages).
International Search Report issued in PCT/US2017/065151 mailed on Jun. 20, 2019 (9 pages).
International Search Report issued in PCT/US2017/065150 mailed on May 14, 2018 (5 pages).
Written Opinion issued in International Application No. PCT/US2017/065150 mailed on May 14, 2018 (10 pages).

* cited by examiner

ARTIFICIAL MUSCLE ACTUATORS

CROSS-REFERENCE TO RELATED APPLICATIONS

This application is a Divisional of U.S. patent application Ser. No. 16/467,830, filed Jun. 7, 2019, which is a National Stage Entry of International Application No. PCT/US2017/065127, filed Dec. 7, 2017, which claims priority, pursuant to 35 U.S.C. § 119(e) to U.S. Provisional Application 62/431,717 filed on Dec. 8, 2016, and U.S. Provisional Application 62/462,544 filed on Feb. 23, 2017. The entire disclosure of each of the above-identified applications, including the specification, drawings, and claims, is incorporated by reference herein in its entirety.

BACKGROUND OF INVENTION

Thermally driven torsional actuators based on twisted polymeric and carbon nanotube (CNT) fibers and yarns have a wide range of applications. Artificial muscle actuators comprising twisted and/or coiled polymers have the advantage of low cost, high production volume, and design simplicity. Artificial muscle actuators may have advantages over small motors because of the greatly simplified engineering and lower product costs.

SUMMARY

In one aspect, an actuator device in accordance with the present disclosure may include a conducting material and at least one fuse incorporated into the conducting material.

In another aspect, an actuator device in accordance with the present disclosure may include an artificial muscle fiber and a thermocouple.

In another aspect, an actuator device in accordance with the present disclosure may include an artificial muscle and a metal tube disposed around a portion of the artificial muscle, wherein the metal tube is crimped to flatten and compress the artificial muscle with the result of securing the muscle relative to the metal tube.

In another aspect, an actuator device in accordance with the present disclosure may include at least one artificial muscle fiber and carbon nanotube yarn, wherein, the carbon nanotube yarn supplies electric current to actuate the at least one artificial muscle fiber.

In another aspect, an actuator device in accordance with the present disclosure may include a first fiber, a conducting material, and a coating, wherein the coating coats the first fiber or the conducting material.

In another aspect, an actuator device in accordance with the present disclosure may include a plurality of fibers; and a coating, wherein the coating coats at least one of the plurality of fibers.

In another aspect, an actuator device in accordance with the present disclosure may include a plurality of fibers; a conducting material; and a coating, wherein the coating coats the conducting material.

Other aspects and advantages of the claimed subject matter will be apparent from the following description and the appended claims.

BRIEF DESCRIPTION OF DRAWINGS

Certain embodiments of the disclosure will hereafter be described with reference to the accompanying drawings, where like reference numerals denote like elements. It should be understood, however, that the accompanying figures illustrate the various implementations described herein and are not meant to limit the scope of various technologies described herein.

DETAILED DESCRIPTION

Figure 1:
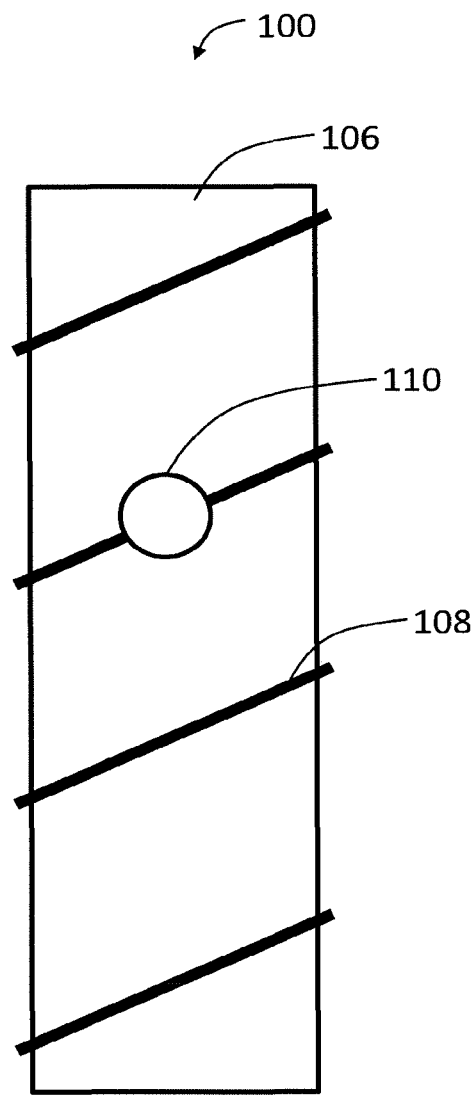
FIG. 1 is a schematic of a fuse in a wire wrapped around an artificial muscle actuator in accordance with one or more embodiments disclosed herein.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Embodiments of the present disclosure will now be described in detail with reference to the accompanying figures. Like elements in the various figures may be denoted by like reference numerals for consistency. Further, it will be apparent to one of ordinary skill in the art that the embodiments disclosed herein may be practiced without the specific details provided to allow a more thorough understanding of the claimed subject matter. Further still, one of ordinary skill in the art will readily recognize that the scale of the elements in the accompanying figures may vary without departing from the scope of the present disclosure.

In general, embodiments of the invention relate to improvements in the structure, fabrication, and operation of artificial muscle actuators. In the embodiments disclosed herein, the actuators include one or more fibers that are thermally driven. In one or more embodiments, the actuators include a conducting material so that the actuation may be stimulated electrically. Embodiments disclosed herein are directed to a fuse-type structure for an artificial muscle actuator, a thermocouple for an artificial muscle actuator, electrical and mechanical contacts for an artificial muscle actuator, and coatings for an artificial muscle actuator. One of ordinary skill in the art will appreciate that the embodiments disclosed herein may be used in combination with other embodiments, or incorporated into other existing actuator technologies, such as those incorporated by reference above.

The term "or" is understood to be an "inclusive or" unless explicitly stated otherwise. Under the definition of "inclusive or," the expression "A or B" is understood to mean "A alone, B alone, or both A and B." Similarly, "A, B, or C" is understood to mean "A alone, B alone, C alone, both A and B, both A and C, both B and C, or A and B and C."

In accordance with embodiments disclosed herein, a carbon nanotube layer is comprised of a plurality of carbon nanotube (CNT) sheets stacked on top of each other. In one or more embodiments, the plurality of CNT sheets may comprise a single sheet wrapped over on itself multiple times. Such CNT sheets may be considered isotropic in accordance with embodiments disclosed herein. In one or more embodiments, these CNT sheets, when stacked on top of each other, become essentially inseparable and cannot be unwrapped. CNT layers in some cases may contain 50 CNT sheets, 100 CNT sheets, or more.

An artificial muscle device may also be referred to as a sheet muscle device, a hybrid nanofiber artificial muscle, a hybrid muscle device, a hybrid actuator, an artificial muscle actuator, or the like.

The term hybrid is used to indicate that CNT sheets are infiltrated with a guest actuation material to form one or more CNT layers, and further that the CNT layers may include other materials as well. For example, materials may include elastomers (e.g., silicone-based rubber, polyurethane, styrene-butadiene copolymer, natural rubber, and the like), fluorinated plastics (e.g., perfluoroalkoxy alkane (PFA), polytetrafluoroethylene (PTFE), fluorinated ethylene propylene (FEP), and the like), aramids, (e.g., Kevlar, nomex, and the like), epoxies, polyimides, paraffin wax, and the like.

In embodiments disclosed herein, a yarn is a long, continuous length of interlocked fibers. In a CNT yarn, the fibers are CNTs, and a core fiber is the fiber around which CNT layers are wrapped.

Embodiments of the invention include actuator materials, or artificial muscles, including twist-spun nanofiber yarn and twisted polymer fibers that generate torsional and/or tensile actuation when powered electrically, photonically, thermally, chemically, by absorption, or by other means. Embodiments of the invention include actuators that utilize coiled yarns or polymer fibers and may be either neat or include a guest.

Artificial muscle actuators may be in the form of straight monofilament, braid monofilament, and coiled monofilament.

The artificial muscle actuator may be in an array of artificial muscle actuators.

The artificial muscles used may be designed to produce linear motion or rotational motion. The artificial muscles may be twisted, and they may be coiled.

Embodiments of the invention may include actuator materials, or artificial muscles, including twist-spun nanofiber yarn and twisted polymer fibers that generate torsional and/or tensile actuation when powered electrically, photonically, thermally, chemically, by absorption, or by other means. Artificial muscles that produce torsional actuation may be known as rotational artificial muscles. Artificial muscles that produce tensile actuation may be known as linear artificial muscles. In one or more embodiments, actuators may utilize coiled yarns or polymer fibers and may be either neat or include a guest material, sometimes referred to as a guest. In one or more embodiments, the guest material may be a guest actuating material.

In one or more embodiments, a fuse-type component may be incorporated into an artificial muscle actuator. In other words, a means may be incorporated into the artificial muscle actuator to avoid a catastrophic failure. In one or more embodiments, as shown in FIG. 1, an artificial muscle fiber device 100, also referred to as an artificial muscle actuator, comprising an artificial muscle fiber 106 may include conducting material 108 where a portion of the conducting material 108 may be replaced with a fuse material 110. The fuse material 110 may be designed to melt and stop electric current flow at a specific temperature or before the glass transition temperature of the artificial muscle fiber 106 is reached. In such embodiments, the artificial muscle fiber 106 may maintain its shape, but may otherwise be non-functional. That is, the artificial muscle fiber 106 may fail in a controlled manner, not catastrophically. The artificial muscle fiber 106 may then be replaced. With replacement, the device incorporating the artificial muscle may be operational again. As represented in FIG. 1, the conducting material may be a metal wire. However, other conducting materials may also be used and the conducting material's shape and positioning relative to the artificial muscle fiber may differ as well.

In accordance with one or more embodiments, the fuse 110 may be composed of common soldering alloys, or any material suitable for a fuse with a melting temperature below that of the artificial muscle fiber 106. Common solder alloys that may be used in a fuse include alloys of tin and lead, and lead-free alloys including either one or more of tin, copper, silver, bismuth, indium, zinc, antimony, germanium, nickel, or the like. For example, the fuse material may melt very quickly at a specific temperature, and/or heat quickly with an applied electrical current. The fuse materials may be selected for the heat tolerance of the material used for the artificial muscle actuating fiber. For example, artificial muscle materials with a higher glass transition temperature may be used in a fuse with higher melting point. Artificial muscle materials with a lower glass transition temperature may have a fuse with a lower melting point.

The fuse material may be added to the artificial muscle in a variety of ways in accordance with embodiments disclosed herein. For example, a section of the conductive material 108 winding around an artificial muscle fiber 106 may be replaced with a conductive fuse material 110. In accordance with embodiments disclosed herein, the conducting material 108 may be incorporated as a drop, a complete coating, or a wire. The fuse material may also be incorporated into the manufacturing of the artificial muscle fiber 106. For example, a conductive wire 108 may be used as the conducting material and wound around the artificial muscle fiber(s) except for one piece of the artificial muscle fiber length. The fuse material may then be placed at this piece of the artificial muscle fiber. One of ordinary skill in the art will appreciate that multiple fuses may be incorporated into an artificial muscle actuation device in accordance with embodiments disclosed herein.

In one or more embodiments, the fuse 110 may be composed of a material that may re-harden. In such embodiments, the material may be electrically conductive when hard, so that the artificial muscle fiber is not rendered unusable after the fuse is blown. In one embodiment, a means to trap the fuse material may be used so that, when the fuse material melts, it retains the same position and does not flow away. The fuse material may be electrically conducting when not melted. For example, a fuse comprised of solder with a non-conducting material with a higher melting point encasing the fuse material may be used in accordance with embodiments disclosed herein. In such embodiments, the fuse may melt, losing conductivity, but still retain its position for when the temperature drops, and the fuse may re-harden and become conductive again.

In one or more embodiments, a type of fuse material that does not melt and is not destroyed may be used. Such a material/device may be designed to effectively prevent electric current from flowing when a specific temperature is exceeded, but may regain its conductivity when the temperature falls below the threshold temperature.

Figure 2:
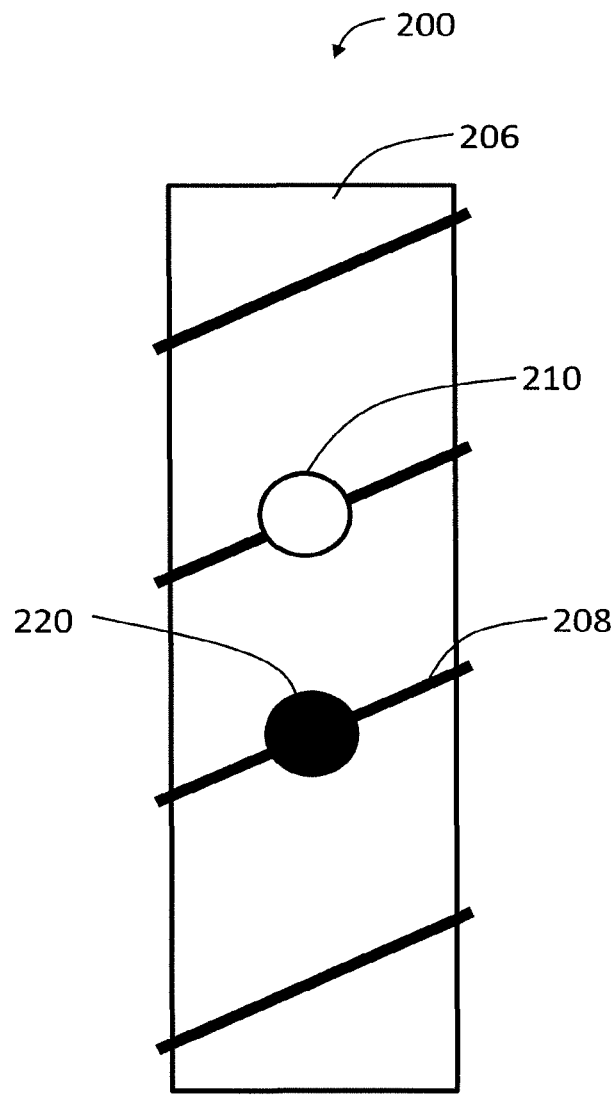
FIG. 2 is a schematic of a self-sensor in an artificial muscle actuator in accordance with one or more embodiments disclosed herein.

As seen in FIG. 2, in one or more embodiments, the artificial muscle actuator 200 may include a series of electronics (not shown) which self-sense whether the artificial muscle actuator has blown a fuse 210. The electronics may include a sensor 220. The electronics may then alert the user to the artificial muscle actuator 200 with a blown fuse 210. The user may then replace the artificial muscle actuator or one or more artificial muscle fibers as desired. In one or more embodiments, the electronics may monitor the temperature of the artificial muscle actuator 200. The electronics may monitor the current flowing through conductive wire 208 wrapped around the artificial muscle fiber 206.

Artificial muscles comprising twisted and/or coiled polymers have the advantage of low cost, high production volume and design simplicity. Hitherto artificial muscles required electronic systems to manage the temperature of the artificial muscle fiber to prevent a catastrophic failure. If the electronic systems fail or be undesirable, there was no way to adequately prevent a failure of the muscle fibers due to accidental overheating. Excessive heat may be incurred due to unexpected environmental conditions, for example high ambient temperature, or it may be due to a failure in the electronics causing excessive current to flow through the artificial muscle. For applications requiring that such a catastrophic failure does not occur, a means may be created within the artificial muscle fiber itself to avoid a catastrophic failure.

In one or more embodiments, artificial muscle materials may include polymeric anisotropic fibers, CNT yarns, or any other suitable material. In one or more embodiments, the artificial muscle actuator may comprise a nylon fiber twisted into a coiled shape with small metal wire wound around the nylon to provide electrical conductivity. Advantageously, nylon is relatively abundant and low in price. Other materials may be desired for their greater actuation speeds, the ability to withstand higher temperatures, greater durability and precision, among other traits. These materials may include polymers, or other materials.

The small metal wire may comprise copper, stainless steel, tungsten, or the like. In one or more embodiments, the artificial muscle actuators are activated with application of heat supplied by applying a voltage across the artificial muscle material. Other heating techniques may include induction heating. For induction heating, it would be necessary to make the conductive material entirely of the fuse material, so that it will melt at a specific temperature, and wholly cease to conduct electricity.

In one or more embodiments, the fuse may be comprised of recoverable fuse material. That is, the fuse may comprise a material which can re-harden and be electrically conductive so that the artificial muscle fiber is not rendered unusable after the fuse is activated.

Figure 3:
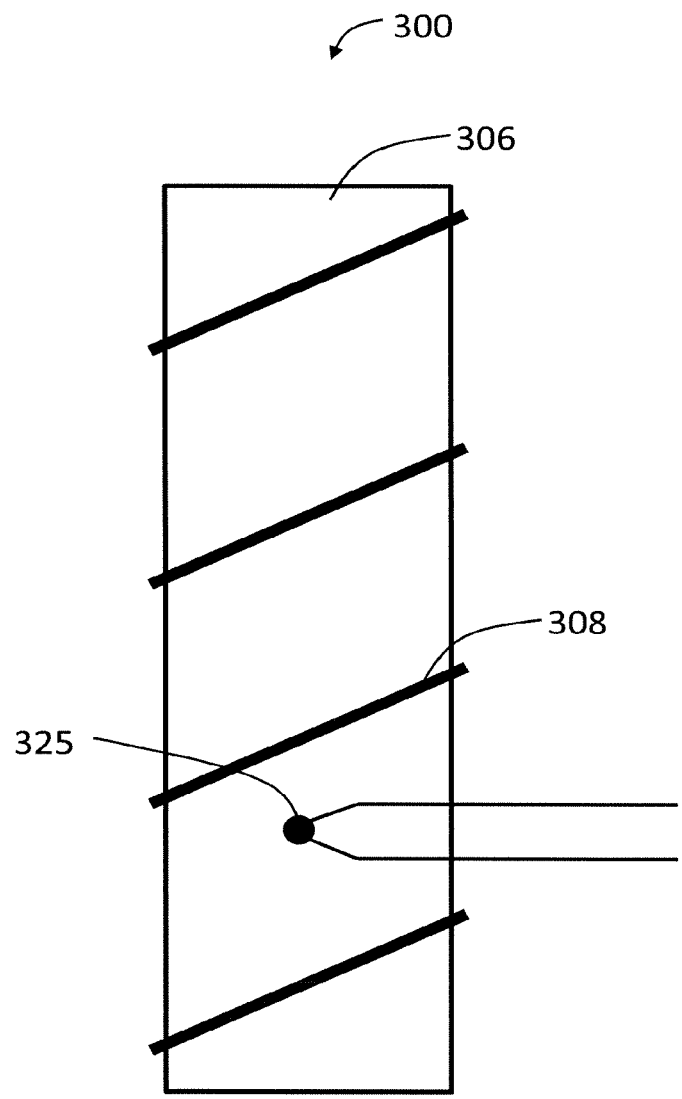
FIG. 3 is a schematic of a thermocouple in an artificial muscle actuator in accordance with one or more embodiments disclosed herein.

In one or more embodiments, as shown in FIG. 3, an artificial muscle actuator 300 may comprise a thermocouple 325 to monitor the temperature of the actuator 300, or an artificial muscle fiber 306, including during actuation. In one or more embodiments, a conductive material 308 may initiate activation of the artificial muscle actuator 300 when an electrical current is passed through it, generating heat. In one or more embodiments, the conductive material 308 may be a small metal wire wrapped around one or more artificial muscle fibers 306. The thermocouple 325 may prevent the artificial muscle actuator 300 from reaching a temperature that may cause damage in accordance with one or more embodiments disclosed herein. Embodiments of an artificial muscle actuator 300 may include a mechanical accumulator, or catapult-type, actuator device. In a mechanical accumulator actuator, an artificial muscle may be actuated but prevented from moving, either rotationally or translationally, by a latching mechanism.

In one or more embodiments, the thermocouple may be incorporated into the means by which the actuation is initiated. For example, if the actuator is electrically driven, the thermocouple may be incorporated into the overall electrical system. In these embodiments, the thermocouple may be integrated into the operation of the actuators, such as in a feedback mechanism or a specific temperature based application.

In one or more embodiments, a thermocouple may be inserted into a bundle of artificial muscle fibers to measure the temperature. Advantageously, the thermocouple may be incorporated with an electronic system to prevent the muscle from reaching a temperature that may cause damage as mentioned previously.

One or more embodiments of the invention are directed to the incorporation of mechanical and electrical contacts into artificial muscle fiber actuators.

In one or more embodiments, the actuators may include a conducting material so that the actuation may be stimulated electrically. This conducting material may be incorporated into a bundle of artificial muscle fibers, coating the individual fibers, or combinations thereof.

Artificial muscles exert large forces relative to their size and mass. One or more embodiments may comprise a means to secure the artificial muscles to mechanical contacts and to provide durable electrical contacts.

In one or more embodiments, a clamp maybe used to mechanically hold muscle fibers together in a bundle, and simultaneously provide electrical contacts. In some embodiments, the mechanical contact may be provided to physically attached to a device holding the muscle fiber. In one or more embodiments, a gold coating may be applied to provide an enhanced electrical and mechanical contact with the addition of the gold coating.

Artificial muscles, also referred to as artificial muscle actuators, may exert large forces for their size and mass. It is necessary to devise a means to secure the artificial muscles to mechanical contacts and to provide durable electrical contacts to the artificial muscles.

Currently existing means of securing artificial muscles to mechanical contacts and providing them with electrical contacts suffer from degradation and loss of electrical and/or mechanical contact with time. A common example of mechanical degradation and failure would be a screw unwinding itself with time and repeated stresses. In addition, artificial muscle may become loose as frames used to hold the artificial muscle may warp over time because of the high stresses applied by the artificial muscles fibers.

Electrical contacts with an artificial muscle may also degrade and/or fail with time. As an example, solder readily breaks under repeated stress and strain, causing a failure in the electrical contact.

In addition, metal wires cannot withstand repeated flexural stresses reliably. A common solution in industry is to extend the length of the metal wire, thereby reducing the angle that each point must bend. However, this approach is unacceptable for the artificial muscles because one of primary advantages artificial muscle actuators over motors is their small fiber-like dimensions. A long metal wire would increase those dimensions.

In one or more embodiments, CNT yarns may not suffer significant damage from repeated stresses. Thus, CNT yarns may be desirable to replace metal wires in supplying current to the muscle fiber and possibly supplying the electrical contact (if pressure is provided from the mechanical contacts). In one or more embodiments, conductive material may be coated on the muscle or inserted in a muscle bundle composed entirely of CNT yarns.

In one or more embodiments, a coating of gold may be applied to a mechanical contact. The gold coating may improve the electrical contact and conductivity of the mechanical contact.

In one or more embodiments, one or more clamps may be used to hold muscle fibers together in a bundle, and simultaneously provide electrical contact. Mechanical contact may also be provided if the clamps are physically attached to the device holding the muscle fiber.

Screws may initially provide adequate mechanical compression to hold artificial muscle fiber in place. However, over time and with repeated actuation from the artificial muscles, the screws will loosen.

A common industrial method for providing secure mechanical and electrical contact is a combination of springs and a baseplate. A spring may be used to compress a segment of the muscle fiber to a baseplate. The baseplate may also function as an electrical contact. While this combination may be more durable than the screw option, it suffers from increased bulk and complexity.

In one or more embodiments, another artificial muscle may replace the springs in the spring and baseplate approach. If the mechanical contact securing the first artificial muscle loosens, the second muscle may be activated to increase the pressure and secure the first muscle.

Figure 4:
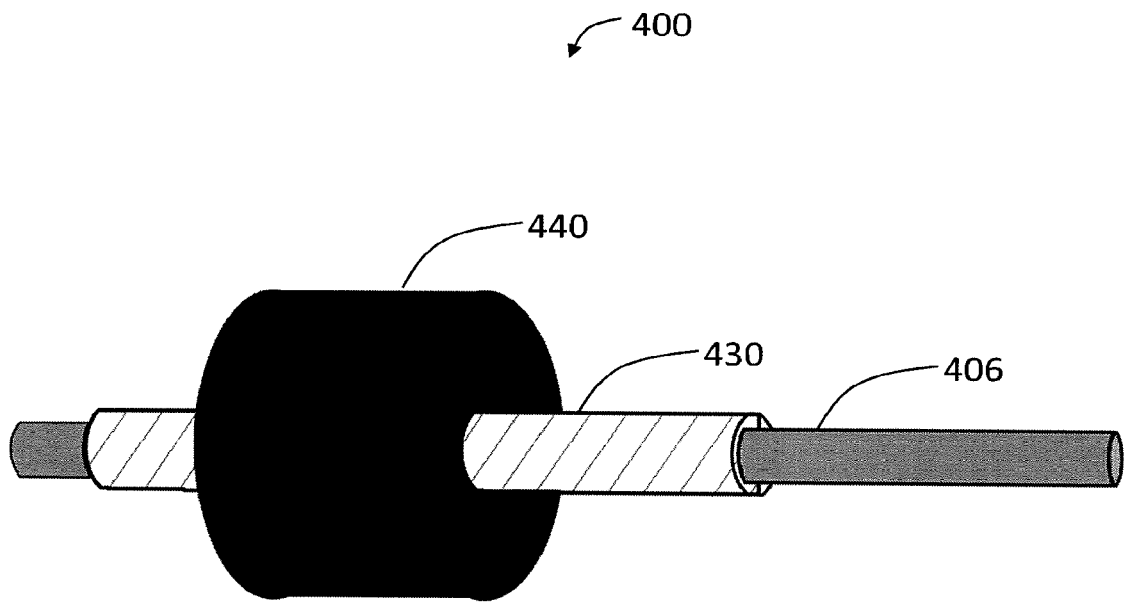
FIG. 4 is a schematic of a clamp in an artificial muscle actuator in accordance with one or more embodiments disclosed herein.

As shown in FIG. 4, in one or more embodiments, a method to secure mechanical and electrical contact to an artificial muscle 406 may comprise fitting a small metal tube 430 around the end of the artificial muscle 406 and crimping the tube 430 to flatten and compress the artificial muscle 406 and secure the muscle tightly. Advantageously, the method is simple and effective. In one or more embodiments, the metal tube 430 may be securely attached onto the muscle 406, but not anything else. The metal tube may be secured to a substrate (not shown) by a clamp 440 or any of the other methods described above to secure an artificial muscle. Also, the orientation of the artificial muscle can be adjusted by loosening the clamp and adjusting the relative orientation of the artificial muscle.

Artificial polymer muscles lacking a protective layer are exposed to the environment. For example, nylon, a particularly useful artificial muscle material, may be susceptible to degradation in the presence of water. Over time, nylon artificial muscle fibers may fail in such environments. Also, nylon may be sensitive to exposure to electromagnetic radiation. In order to protect the artificial muscle fiber, it may be advantageous to apply a coating onto the fiber surface.

In general, one or more embodiments relate to a thin coating in an artificial muscle to protect the artificial muscle and, in some cases, enhance the properties of the artificial muscle. In the embodiments disclosed herein, the actuators may include one or more fibers that are thermally driven. In one or more embodiments, the actuators may include a conducting material so that the actuation may be stimulated electrically. In other words, an applied voltage or current may provide the necessary temperature changes for actuation. Embodiments of the coating layer may protect the artificial muscle fiber, and may improve characteristics of the produced artificial muscle or actuator.

For example, in one or more embodiments, a black colored coating can be applied so that the artificial muscle or actuator readily absorbs radiation. Such radiation may be used in the function of the actuator. In one or more embodiments, a coating may be selected that is suitable to interact closely with biological material.

As another example, in one or more embodiments the coating may be reflective. A reflective muscle may be able to maintain exposure to the sun without heating too far above the temperature of the surrounding environment.

In one or more embodiments, a coating may be thermally conducting. In such embodiments, the coating may enable heat to be more easily whisked away from the artificial muscle fiber, which may improve stroke efficiency and possibly prevent any defective spots in the fiber from overloading with heat. Such "hot spots" may be caused by a conductor material in the artificial muscle or the actuator having imperfections along the length of the artificial muscle fiber. If such hot spots are not addressed, there is a danger that the polymer fiber along that section will overheat and melt, resulting in a failure of the muscle.

In one or more embodiments, the coating material may be designed to lend new properties to the artificial muscle fiber. In one or more embodiments, the coating material may be designed to protect the artificial muscle from environmental conditions. In some embodiments, the coating may serve to protect the conductor material and/or protect the polymer fiber.

In or more embodiments, the coating may be multifunctional. For example, the coating may be designed to enhance the thermal properties, provide adhesion or reduce friction, and protect from, or incorporate into, the surrounding environment. Embodiments of the invention may include multi-functional coatings that may be engineered for any combination of the above characteristics depending on the specific application for the artificial muscle actuator.

In one or more embodiments, the coating may be selected to interact well with biological material, making the artificial muscles useful for incorporation into devices in the human body. In these embodiments, care must be taken to ensure adequate thermal dissipation to prevent burn damage to the biological material.

In one or more embodiments, the coating may provide electrical insulation to the conductor material and/or protect the polymer fiber. Such embodiments may be useful in artificial muscles that include a bundle of artificial muscle fibers forming the artificial muscle (or actuator).

In one or more embodiments, the coating may be designed to reduce surface friction. Such embodiments may also be useful in artificial muscles that include a bundle of fibers forming the artificial muscle (or actuator). For example, the low surface tension of parylene as a coating material may increase slippage between the muscle fibers within a bundle. Such embodiments may be useful in creating tighter bundles of smaller fibers.

In one or more embodiments, the coating may be designed for protection from the environment. For example, moisture protection, UV radiation protection, oxidation protection, saline solution protection, and/or high temperature protection. Embodiments of the artificial muscle or actuator that include one or more metal wires may particularly benefit from saline protection. Embodiments that include high temperature protection may also protect the external environment from the high temperature of the conductive material, and/or protect the muscle fiber from sudden changes in external temperature. Embodiments of the invention may adjust the color of the muscle to black to increase the emission of thermal radiation, which may increase the efficiency of the muscle.

In one or more embodiments of the invention, the structure of the coated artificial muscle fiber may be similar to that of a real muscle fiber in that there is a protective layer coating each muscle fiber that makes up the artificial muscle. In one or more embodiments, the protective coating may also be a layer coating the entire artificial muscle or actuator. In one or more embodiments, the coating may be uniform, with no punctures or defects that may allow the external environment to directly contact the artificial muscle fiber.

Figure 5:
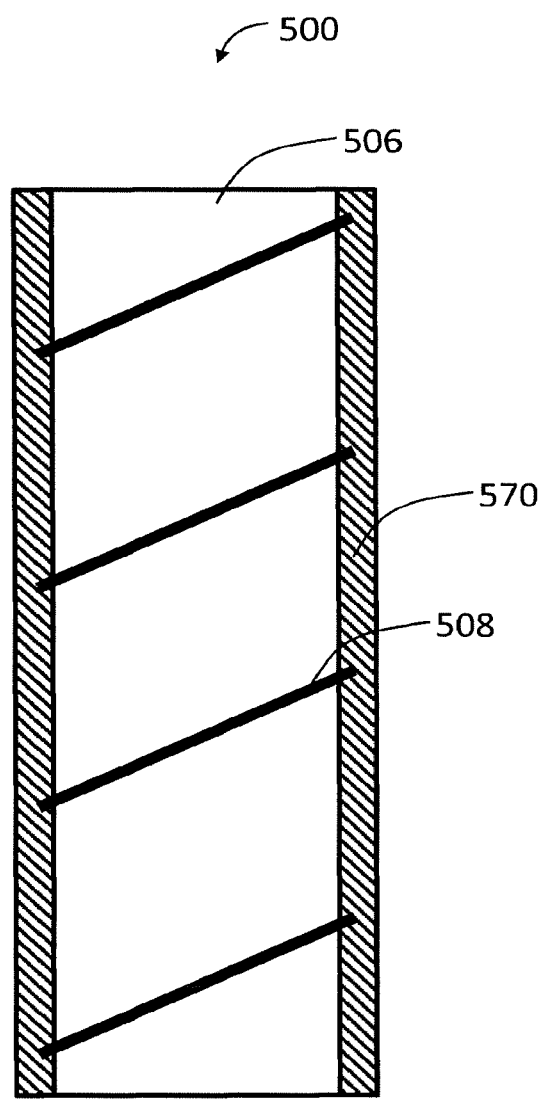
FIG. 5 is a schematic of a coating in an artificial muscle actuator in accordance with one or more embodiments disclosed herein.

As shown in FIG. 5, an artificial muscle or actuator 500 may include a metal wire 508 incorporated as a conductor material. In such embodiments, it may be advantageous for the protective coating 570 to completely cover the metal wires 508. It may also be necessary that the metal wires do not separate from a surface of the artificial muscle fiber 506 that makes up the artificial muscle or actuator 500. During the coating process, care must be taken not to insulate the metal wire 508 from the surface of the artificial muscle fiber 506. Such insulation may negatively affect the performance of the artificial muscle fiber 506.

In one or more embodiments of the invention, a selective polyurethane coating may be used on metal wires included in the artificial muscle or actuator. For example, the conductive metal wire that is incorporated into the artificial muscle fiber may be pretreated with a polymer useful for coating the muscle fibers and the wire. Then, the polymer coating of the metal wire may be further melted to coat, or partially coat, the artificial muscle fiber. In such embodiments, the coating may be primarily deposited in areas close to the metal wires, leaving some areas of the polymer muscle fiber exposed. This selective coating may be useful in protecting the wires while intentionally leaving some of the muscle fibers exposed. In one or more embodiments, the selective coating may be used in combination with another coating layer, to provide greater protection for areas closer to the conductive wires.

Various polymers may be used for the coating, for example, parylene, polyurethane, polyvinyl based polymers, and fluorinated polymers in accordance with one or more embodiments disclosed herein. In one or more embodiments, the coating may be metal. For example, gold, silver, titanium, copper, nickel, and mixtures thereof may be used. In one or more embodiments, alloys of the above metals, or for example, chromium may be used. In one or more embodiments, a metal wire incorporated into the artificial muscle may be coated with polyurethane. In one or more embodiments, the wire may be wrapped around the artificial muscle fibers and heated to melt the polyurethane to the muscle fiber surface. In such embodiments, more polyurethane may be added to completely coat the artificial muscle or actuator. In one or more embodiments, nano-composites, such as nanostructured clay in a polymer or graphene dispersed in a polymer, may be used as a coating material. Such embodiments may be advantageous for conducting heat and ensuring proper heat dissipation.

In general, the process for depositing the coating may include sputtering, electroplating, chemical vapor deposition (CVD), solution based deposition, and other techniques for producing a film or coating as known in the art. It may be necessary to coat the artificial muscle fibers after they have been twisted and/or coiled because the coating may be damaged in the twisting and/or coiling process. However, some embodiments may be coated prior to the twisting/coiling process. For example, silver-coated nylon may be used in artificial muscle fabrication to provide a coating incorporated prior to the twisting/coiling process.

In one or more embodiments, a polyurethane coated metal wire may be used as a conductor in the artificial muscle or actuator. The polyurethane on the wire may be further melted so that the polyurethane covers at least a portion of the artificial muscle fiber. Another coating of the same or different material may be subsequently applied onto the surface of the artificial muscle fiber in accordance with one or more embodiments.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An actuator device comprising:
    at least one or more artificial muscle fibers, the at least one or more artificial muscle fibers being twisted and coiled;
    a thermal conductive material, the thermal conductive material being wrapped around the at least one or more artificial muscle fibers;
    a thermocouple, the thermocouple being incorporated into the at least one or more artificial muscle fibers, and
    an electrical system, wherein
    twisting of the at least one or more artificial muscle fibers causes the coiling of the at least one or more artificial muscle fibers;
    the thermocouple monitors a temperature of the at least one or more artificial muscle fibers; and
    the electrical system actuates the at least one or more artificial muscle fibers by electrically heating the thermal conductive material and managing the temperature not to exceed a threshold temperature to prevent failure of the artificial muscle actuator device.

2. The actuator device of claim 1, wherein the thermal conductive material is a carbon nanotube yarn.

3. The actuator device of claim 1, wherein the at least one or more artificial muscle fibers comprise carbon nanotube yarns.

4. The actuator device of claim 1, further comprising: a coating, wherein the coating coats the at least one or more artificial muscle fibers or the thermal conductive material.

5. The actuator device of claim 4, wherein the coating provides at least one of the following properties: moisture protection, UV protection, thermal insulation and thermal conductivity.

6. The actuator device of claim 4, wherein the coating prevents oxidation.

7. The actuator device of claim 4, wherein the coating protects the at least one or more artificial muscle fibers and the thermal conductive material from exposure to saline.

8. The actuator device of claim 4, wherein the coating is a black colored coating.

9. The actuator device of claim 4, wherein the coating is biocompatible.

10. The actuator device of claim 4, wherein the coating is electrically insulating.

11. The actuator device of claim 4, wherein the coating coats each of the at least one or more artificial muscle fibers.

12. The actuator device of claim 4, wherein the coating reduces surface friction between the plurality of fibers.

13. The actuator device of claim 4, wherein the thermal conductive material is a metal wire, and the coating encloses the metal wire.

14. The actuator device of claim 4, wherein the coating provides adhesion between the thermal conductive material and the at least one or more artificial muscle fibers.

15. The actuator device of claim 4, wherein the coating includes at least one of the following materials: parylene, polyurethane, gold, silver, titanium, copper, nickel, chromium, nanostructured clay in a polymer, graphene dispersed in a polymer, and fluorinated polymers.

16. The actuator device of claim 4, wherein the coating is multi-functional.

17. The actuator device of claim 4, where the coating is reflective.

18. The actuator device of claim 1, wherein the at least one or more artificial muscle fibers comprise polymer fibers.

* * * * *